United States Patent [19]

Carenzi et al.

[11] Patent Number: 4,560,696
[45] Date of Patent: Dec. 24, 1985

[54] ANALGESIC, ANTIPYRETIC OR ANTI-INFLAMMATORY IMIDAZOLE COMPOUNDS

[75] Inventors: Angelo Carenzi, Busto Arsizio; Dario Chiarino, Monza; Davide Della Bella, Milan; Viviana Frigeni, Monza; Carlo Veneziani, Bresso, all of Italy

[73] Assignee: Zambon S.p.A., Milan, Italy

[21] Appl. No.: 591,243

[22] Filed: Mar. 20, 1984

Related U.S. Application Data

[63] Continuation of Ser. No. 403,123, Jul. 29, 1982, abandoned.

[30] Foreign Application Priority Data

Jul. 31, 1981 [IT] Italy ................ 23270 A/81

[51] Int. Cl.$^4$ .................. A61K 31/415; C07D 233/64
[52] U.S. Cl. .................... 514/397; 514/400; 548/336; 548/342
[58] Field of Search .............. 548/342, 336; 424/273 R; 514/397, 400

[56] References Cited

U.S. PATENT DOCUMENTS

| | | | |
|---|---|---|---|
| 4,104,473 | 8/1978 | Sawa et al. | 548/342 |
| 4,119,781 | 10/1978 | Lewis et al. | 548/342 X |
| 4,122,277 | 10/1978 | Sawa et al. | 548/342 |
| 4,124,766 | 11/1978 | Paul et al. | 548/342 X |
| 4,139,708 | 2/1979 | Labaw et al. | 548/342 |
| 4,292,431 | 9/1981 | Kim et al. | 548/342 |

OTHER PUBLICATIONS

*Chemical Abstracts*, 92:181184f (1980) [Jpn. Kokai, 79, 141, 771, Nishimura, 11/5/79].

*Primary Examiner*—Richard A. Schwartz
*Attorney, Agent, or Firm*—Stevens, Davis, Miller & Mosher

[57] ABSTRACT

New imidazole compounds of the formula

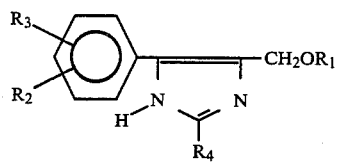

their salts and analgesic, antipyretic and antiinflammatory pharmaceutical composition containing them. New intermediates useful in the preparation of said imidazole compounds.

Process for preparing the new imidazole compounds as well as some new intermediates for the preparation thereof.

5 Claims, No Drawings

ANALGESIC, ANTIPYRETIC OR ANTI-INFLAMMATORY IMIDAZOLE COMPOUNDS

This application is a continuation of application Ser. No. 403,123, filed July 29, 1982, now abandoned.

This invention relates to new imidazole compounds endowed with analgesic, antipyretic, antiinflammatory activity, to the pharmaceutically acceptable salts thereof, to the pharmaceutical compositions containing them and to some intermediates useful for the preparation of the new imidazole compounds.

A further object of this invention is the process for preparing the new imidazole compounds as well as some intermediates useful for their preparation. More particularly, the compounds of this invention have the formula

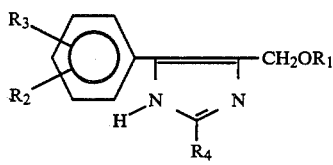

(I)

wherein $R_1$ is selected from the group comprising a straight or branched chain alkyl having from 1 to 10 carbon atoms, cycloalkyl having from 3 to 6 carbon atoms, aryl, substituted aryl, arylalkyl, substituted arylalkyl, heterocycle, substituted heterocycle, alkylheterocyclic, substituted alkylheterocycle, acyl and aroyl, $R_2$ and $R_3$ are the same or different and each is selected from the group comprising hydrogen, halogen, hydroxyl, straight or branched chain alkyl having from 1 to 4 carbon atoms, alkoxyl having from 1 to 4 carbon atoms, alkylthio, aklylsulfonyl; or $R_2$ and $R_3$ together represent an aromatic ring condensed with phenyl, $R_4$ is hydrogen, aryl or substituted aryl.

Typical instances of the compounds of the general formula (I) are:
4-ethoxymethyl-5-phenyl-imidazole
4-ethoxymethyl-5-(4-methoxyphenyl)-imidazole
4-ethoxymethyl-5-(4-methylphenyl)-imidazole
4-ethoxymethyl-5-(2-naphthyl)-imidazole
4-ethoxymethyl-5-(3-chlorophenyl)-imidazole
4-ethoxymethyl-5-(2-chlorophenyl)-imidazole
4-ethoxymethyl-5-(2-methoxyphenyl)-imidazole
4-ethoxymethyl-5-(4-methylthiophenyl)-imidazole
4-ethoxymethyl-5-(4-methylsulfonylphenyl)-imidazole
4-ethoxymethyl-5-(4-chlorophenyl)-imidazole
4-ethoxymethyl-5-(3-methoxyphenyl)-imidazole
4-ethoxymethyl-5-(3,4-dimethoxyphenyl)-imidazole
4-cyclohexyloxymethyl-5-(4-chlorophenyl)-imidazole
4-isopropoxymethyl-5-(4-chlorophenyl)-imidazole
4-ethoxymethyl-2,5-diphenyl-imidazole
4-methoxymethyl-5-(4-chlorophenyl)-imidazole
4-n-butoxymethyl-5-(4-chlorophenyl)-imidazole
4-benzyloxymethyl-5-(4-chlorophenyl)-imidazole
2-phenyl-4-ethoxymethyl-5-(4-chlorophenyl)-imidazole
bis-[(5-phenyl-imidazol-4-yl)-methyl]-ether
4-phenoxymethyl-5-(4-chlorophenyl)-imidazole
4-(4-chlorophenoxy)-methyl-5-(4-chlorophenyl)-imidazole
4-(2-methylphenoxy)-methyl-5-(4-chlorophenyl)-imidazole
4-(2,3-dimethylphenoxy)-methyl-5-(4-chlorophenyl)-imidazole
4-(2-methoxyphenoxy)-methyl-5-(4-chlorophenyl)-imidazole
2-phenyl-4-phenoxymethyl-5-(4-chlorophenyl)-imidazole The compounds having formula (I) may be prepared from the corresponding alcohols of the formula

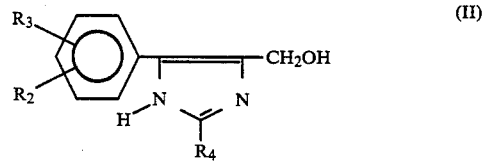

(II)

(wherein $R_2$, $R_3$ and $R_5$ have the above indicated meanings).

The alcohols of the formula (II) are new and are a further object of the present invention.

Typical instances of the compounds of the general formula (II) are:
4-hydroxymethyl-5-phenyl-imidazole
4-hydroxymethyl-5-(4-methylphenyl)-imidazole
4-hydroxymethyl-5-(2-naphthyl)-imidazole
4-hydroxymethyl-5-(3-chlorophenyl)-imidazole
4-hydroxymethyl-5-(2-chlorophenyl)-imidazole
4-hydroxymethyl-5-(2-methoxyphenyl)-imidazole
4-hydroxyphenyl-5-(4-methylthiophenyl)-imidazole
4-hydroxymethyl-5-(4-methylsulfonylphenyl)-imidazole.
4-hydroxymethyl-5-(4-chlorophenyl)-imidazole
4-hydroxymethyl-5-(3,4-dimethoxyphenyl)-imidazole
4-hydroxymethyl-5-(3-methoxyphenyl)-imidazole
2,5-diphenyl-4-hydroxymethyl-imidazole The process according to this invention comprises essentially the reaction of a product of the formula (II) or of a reactive derivative thereof with a product of the formula HO-$R_1$, where $R_1$ has the above mentioned meanings, or with a reactive derivative thereof, to afford a product of the formula (I) or an acid addition salt thereof and, optionally, the treatment of the thus obtained salt with a base to give the product of the formula (I) which may be then treated with a pharmaceutically acceptable acid to afford a pharmaceutically acceptable acid addition salt.

The alcohols of the formula (II) may be prepared by reducing the compounds of the formula

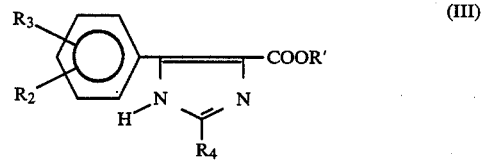

(III)

wherein R' is hydrogen or alkyl and $R_2$, $R_3$ and $R_4$ have the above mentioned meanings.

Typical instances of the compounds of the general formula (III) are:
4-carbethoxy-5-phenyl-imidazole
4-carbethoxy-5-(4-methylphenyl)-imidazole
4-carbethoxy-5-(4-chlorophenyl)-imidazole
4-carbethoxy-5-(2-naphthyl)-imidazole 4-carbethoxy-5-(3-chlorophenyl)-imidazole
4-carbethoxy-5-(2-chlorophenyl)-imidazole
4-carbethoxy-5-(2-methoxyphenyl)-imidazole.
4-carbethoxy-5-(4-methoxyphenyl)-imidazole
4-carbethoxy-5-(3,4-dimethoxyphenyl)-imidazole
4-carbethoxy-5-(3-methoxyphenyl)-imidazole
4-carbethoxy-5-(4-methylthiophenyl)-imidazole
4-carbethoxy-5-(4-methylsulfonyl-phenyl)-imidazole Alternatively the alcohols of the formula (II) wherein $R_4$ is an aryl radical are also obtained by treating a 2,4-phenylimidazole with formaldehyde or a precursor thereof in the presence of a basic compound such as sodium and potassium hydroxyde and of a suitable solvent such as an aliphatic alcohol, preferably at the boiling temperature of the reaction mixture.

Finally, the compounds of the formula (III) wherein $R_4$ is hydrogen may be obtained by condensing the compounds of the formula

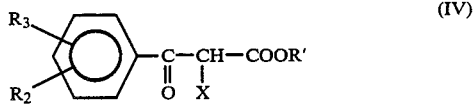

(IV)

wherein X is halogen, $R_2$ and $R_3$ have the above indicated meanings and R' is alkyl, with formamide, in the presence of formic acid, at a temperature comprised between 130° and 160° C.

The preparation of the products of the formula (I) wherein $R_1$ is alkyl, cycloalkyl, aryl, substituted aryl, arylalkyl, substituted arylalkyl, heterocycle, substituted heterocycle, or alkylheterocycle optionally substituted may be performed by treating an alcohol (II) with a suitable halogenating agent, such as a halogen acid, thionyl chloride or thionyl bromide to give the compounds of the formula

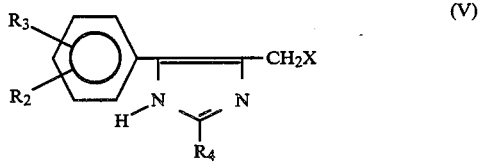

(V)

wherein X is halogen and $R_2$, $R_3$ and $R_4$ have the above mentioned meanings.

The halogenation is preferably performed at the boiling temperature of the reaction mixture and in the presence of an excess of the halogenating agent.

The thus obtained compounds (V) are then reacted with a compound of the formula $R_1OH$ or $R_1OM$ (wherein $R_1$ has the above mentioned meanings and M is a metal, preferably sodium) to afford the corresponding ethers. When it is used a compound of formula $R_1OM$ the reaction is carried out in the presence of a suitable solvent and at a temperature comprised between $-15°$ and the boiling temperature of the reaction mixture. For each mole of compound (V) are added from 1 to 2 moles of compound $R_1OM$.

Alternatively, a compound of formula (V) may be reacted under reflux with an excess of a compound $R_1OH$.

The ethers of the formula (I) may be also prepared by reacting an alcohol of the formula (II) with a compound of formula $R_1OH$, in the presence of a suitable condensing agent such as p-toluensulfonic acid.

The preparation of the products of the formula (I) wherein $R_1$ is an acyl or aroyl radical may be performed according to usual procedures such as esterification of the alcohols of formula (II) with a suitable acid or a reactive derivative thereof.

The reduction of the compounds (III) to alcohols (II) may be carried out with a suitable reducing agent, such as lithium aluminum hydride, sodium borohydride, lithium borohydride. This step is preferably carried out in the presence of an inert solvent such as tetrahydrofurane, benzene, toluene, dioxane, and at a temperature comprised between 40° C. and the boiling temperature of the reaction mixture.

A further object of the present invention are the pharmaceutically acceptable salts of the compounds of formula (I) with organic or inorganic acids.

Among the organic and inorganic salts may be mentioned hydrochloride, hydrobromide, sulfate, phosphate, methanesulfonate, arylsulfonate, maleate, fumarate, citrate, tartrate and benzoate.

The antipyretic, analgesic and antiinflammatory activity of the compounds (I) have been evaluated with several pharmacological tests.

The data reported below have been obtained by testing 4-ethoxymethyl-5-(4-chlorophenyl)-imidazole and 4-phenoxymethyl-5-(4-chlorophenyl)-imidazole (which will be indicated hereinbelow for brevity as Z 1327 and Z 1356 respectively) and are illustrative of the pharmacological profile of all the compounds of the formula (I).

The antipyretic activity has been proved in rats by means of the test of the yeast induced hyperthermy inhibition: $ED_{50}$ of Z 1327 and of Z 1356 are respectively 65 and 30 mg/kg/os and 30 and 25 mg/kg/i.p.

The analgesic activity has been proved in mice by the test of acetic acid induced stretching inhibiton: $ED_{50}$ for Z 1327 is 79 mg/kg/os, whereas $ED_{50}$ for Z 1356 is 55 mg/kg/os.

Finally, the antiinflammatory activity has been proved in rats by the carrageenin oedema test: $ED_{50}$ for Z 1327 is 130 mg/kg/os and 30 mg/kg/i.p., whereas $ED_{50}$ for Z 1356 is 100 mg/kg/os and 25 mg/kg/i.p.

Furthermore, the compounds have been proved to have very little toxicity in mice; in fact $LD_{50}$ of both products after oral administration is higher than 1000 mg/kg, whereas by i.p. route is 400 mg/kg.

This invention also relates to pharmaceutical compositions comprising the compounds of the formula (I) or the salts thereof as active ingredients.

The compositions may contain the active ingredient together with an organic or inorganic solid or liquid pharmaceutical excipient suitable for topical, oral, parenteral or rectal administration. The pharmaceutical compositions may be in solid form such as tablets, dragées, capsules, powders, granular, suppositories, candles, or in liquid form as solutions, suspensions, emulsions, or in semisolid form such as creams, ointments.

They may be also prepared in such a way that the release of the drug is prolonged after the administration.

They may contain the usual carrier materials and may include auxiliary substances such as preserving, stabilizing, wetting or emulsifying agents, salts for regulating the osmotic pressure, buffers, dyestuffs or flavouring agents.

They are prepared according to known methods and may further contain other valuable substances.

All the products described in the examples have been characterized by NMR.

It is not always necessary to isolate and to purify, as described in the following examples, the intermediates; the most part of them, in fact, may be used in the subsequent steps of the process without any previous separation or purification.

The following examples are given to illustrate the present invention without limiting it in any way.

EXAMPLE 1

4-carbethoxy-5-phenyl-imidazole 22.7 g (0.1 mole) of ethyl 2-chloro-3-oxo-3-phenyl propanoate is added dropwise fairly rapidly into a vigorously stirred solution of 2.3 g (0.049 mole) of formic acid and of 7.5 ml of water in 39.8 ml (0.883 mole) of formamide heated at 135°–140° C.

When the addition is complete the reaction mixture is refluxed for 2.5 hours, then it is cooled to about 0° C. and filtered; the precipitate is washed carefully with water until the chloride ion in the aqueous wash is no longer detectable, and then dried at 50°–60° C.

11.7 g (yield 54.1%) of crude product is obtained which is crystallized twice from 96% ethanol to give 8.4 g of pure 4-carbethoxy-5-phenyl-imidazole (yield 36.8%), m.p. 226°–228° C.

In a similar manner the following compounds have been prepared:
4-carbethoxy-5-(4-methoxyphenyl)-imidazole, m.p. 203°–205° C.
4-carbethoxy-5-(3,4-dimethoxyphenyl)-imidazole, m.p. 181°–183° C.
4-carbethoxy-5-(3-methoxyphenyl)-imidazole, m.p. 146°–151° C.
4-carbethoxy-5-(4-methylthiophenyl)-imidazole, m.p. 192°–194° C.;
from this product, by the usual oxidation techniques, the 4-carbethoxy-5-(4-methylsulphonyl-phenyl)-imidazole is obtained, m.p. 211°–213° C.

EXAMPLE 2

4-hydroxymethyl-5-phenyl-imidazole hydrochloride 293.5 g (1.357 mole) of 4-carbethoxy-5-phenyl-imidazole is added portionwise to a suspension of 103 g (2.714 mole) of $LiAlH_4$ in 4500 ml of tetrahydrofurane cooled in a water-bath.

The reaction mixture is heated under reflux for 4.5 hours then is cooled in a water-ice bath and excess hydride is carefully decomposed with 110 ml of water, 110 ml of 15% aqueous NaOH and 330 ml of water.

The resulting suspension is filtered and the solid material on the filter is extracted 2–3 times with warm methanol by centrifuging every time. The methanolic extracts are combined with the preceding tetrahydrofurane filtrate and evaporated.

The residue is taken up in water and acetic acid at pH about 4, and heated with a water-bath until the solution is complete. The reaction mixture is then decolourized with activated carbon, filtered and the filtrate is made basic with a concentrated aqueous solution of $NH_4OH$.

The resulting mixture is cooled, filtered and the precipitate is washed thoroughly with water and dried to yield 213 g (90.2%) of 4-hydroxymethyl-5-phenyl-imidazole, m.p. 174°–175° C. (dec.).

From the thus obtained compound and according to the usual techniques the hydrochloride may be prepared (m.p. 190°–192° C., crystallized from ethanol).

In a similar manner the following compounds may be prepared:
4-hydroxymethyl-5-(4-chlorophenyl)-imidazole hydrochloride; m.p. 165°–168° C. (dec.)
4-hydroxymethyl-5-(3,4-dimethoxyphenyl)-imidazole hydrochloride; m.p. 197° C. (dec.)
4-hydroxymethyl-5-(3-methoxyphenyl)-imidazole hydrochloride; m.p. 130°–134° C.

EXAMPLE 3

2,5-diphenyl-4-hydroxymethyl-imidazole hydrochloride 5 g (0.0227 mole) of 2,4-diphenyl-imidazole, 0.85 g (0.0283 mole) of paraformaldehyde and 0.1 g of finely ground potassium hydroxide are dissolved in 29 ml of warm methanol and heated under reflux for 90 hours.

The solution is then decolourized with activated carbon, filtered and dried.

Water and chloroform are added to the residue by stirring; the insoluble solid of both the layers is filtered, washed with water and chloroform and dried. 2.8 g (yield 49.3%) of crude product is thus obtained, which is crystallized from methanol to afford 1.1 g of 2,5-diphenyl-4-hydroxymethyl-imidazole, m.p. 206°–207° C. (dec.) By the usual techniques the hydrochloride has been obtained, m.p. about 220° C. (dec.).

EXAMPLE 4

4-ethoxymethyl-5-phenyl-imidazole hydrochloride 30 g (0.172 mole) of 4-hydroxymethyl-5-phenyl-imidazole is dissolved in 79 ml of 47% aqueous hydrobromic acid; the solution is stirred vigorously and heated under reflux for 5 hours.

The suspension is allowed to cool in a water-ice bath for 1 hour under stirring, then is filtered.

The precipitate is washed with acetone and ethyl ether and dried under vacuum at room temperature.

48 g (yield 87.6%) of 4-bromo-methyl-5-phenyl-imidazole hydrobromide is obtained.

A solution of 15 g (0.047 mole) of this compound in 500 ml of anhydrous ethanol is cooled to about 0° C. and, a solution of sodium ethylate obtained from 1.1 g (0.0472 mole) of sodium and 50 ml of anhydrous ethanol, is added dropwise under stirring.

The reaction mixture is heated under reflux for 1.5 hours and then evaporated. The residue is dissolved in water made slightly acidic with hydrochloric acid.

After the solution is decolourized with carbon and made basic with a concentrated aqueous solution of $NH_4OH$, it is extracted several times with ethyl ether, then one with ethyl acetate and then finally once with chloroform.

The combined organic extracts are diluted with ethyl ether, decoulorized and evaporated.

100 ml of pentane is added to the residue and the mixture is heated to the boiling temperature. The solid is filtered and dried under vacuum at 50° C. to give 6 g (yield 62.9%) of the title compound which is dissolved in 25 ml of anhydrous ethanol and acidified with a saturated ethanolic solution of hydrochloric acid.

The solution is allowed to stand at about 0° C. a long time, and provides a precipitate which is filtered, washed with acetone and dried under vacuum at 60° C. to give 4.2 g (yield 37.3%) of 4-ethoxymethyl-5-phenyl-imidazole hydrochloride; m.p. 176°–178° C. (dec.).

EXAMPLE 5

4-ethoxymethyl-5-(4-chlorophenyl)-imidazole hydrochloride 12.25 g (0.05 mole) of 4-hydroxymethyl-5-(4-chlorophenyl)-imidazole hydrochloride is added to stirred thionyl chloride (30 ml). The solution is heated to the boiling temperature and stirred for further 2 hours. After cooling to about 0° C. for about 30 min. the reaction mixture is filtered; the solid on the filter is washed with ethyl ether and dried under vacuum to give 12.7 g (yield 96.6%) of 4-chloromethyl-5-(4-chlorophenyl)-imidazole hydrochloride.

65 g (0.247 mole) of this product is dissolved in 780 ml of anhydrous ethanol, the thus obtained solution is heated under reflux and stirred for 24 hours, then is evaporated to dryness to provide 66.3 g of a residue which is crystallized from isopropanol.

58.9 g of pure product is obtained, m.p. 175°–177° C. (dec.); yield 87.4%.

In a manner similar to that described in Examples 4 or 5 the following compounds have been prepared:
4-ethoxymethyl-5-(3-methoxyphenyl)-imidazole hydrochloride, m.p. 148°–149° C.
4-ethoxymethyl-5-(3,4-dimethoxyphenyl)-imidazole hydrochloride, m.p. 180°–182° C.
4-cyclohexyloxymethyl-5-(4-chlorophenyl)-imidazole hydrochloride, m.p. 178°–180° C.
4-isopropoxymethyl-5-(4-chlorophenyl)-imidazole hydrochloride, m.p. 160°–161° C. (dec.)
4-ethoxymethyl-2,5-diphenyl-imidazole hydrochloride, m.p. 168°–170° C. (dec.)
4-methoxymethyl-5-(4-chlorophenyl)-imidazole hydrochloride, m.p. 181°–183° C. (dec.)
4-n-butoxymethyl-5-(4-chlorophenyl)-imidazole hydrochloride, m.p. 158°–160° C.
4-benzyloxymethyl-5-(4-chlorophenyl)-imidazole hydrochloride, m.p. 159°–161° C.
2-phenyl-4-ethoxymethyl-5-(4-chlorophenyl)-imidazole hydrochloride, m.p. 260° C.

EXAMPLE 6

Bis-[(5-phenyl-imidazol-4-yl)-methyl]-ether dihydrochloride 26 g (0.1468 mole) of p-toluensulfonic acid monohydrate in 1500 ml of toluene is anhydrified by distillation.

The resulting solution is cooled and added all at once with 20.1 g (0.1144 mole) of 4-hydroxymethyl-5-phenyl-imidazole and 700 ml of toluene then again is heated to the boiling temperature. The reaction mixture is distilled and stirred for further 4 hours, while toluene is slowly added in order to keep constant the volume of the mixture. The mixture is then distilled for further 1.5 hours without adding toluene and a solid product separates. The suspension is diluted with ether and is shaken with an amount of aqueous solution of sodium hydroxide suitable to neutralize p-toluensulfonic acid.

The aqueous layer is discarded, whereas the organic layer is decanted. The solid residue is dissolved in 10% hydrochloric acid. The organic layer is extracted once or twice with 10% hydrochloric acid.

The combined aqueous extracts are decolourized with activated carbon and made basic with a diluted aqueous solution of NH4OH. The thus obtained precipitate is filtered, washed several times with water, air dried, dissolved in 700 ml of methanol, decolourized with activated carbon and filtered. The evaporation of the methanolic solution affords 16.7 g of a solid product (yield 88.4%).

This product is suspended in 50 ml of anhydrous ethanol, neutralized with a suitable amount of saturated ethanolic solution of hydrochloric acid (10–11 ml) and crystallized from ethanol to yield 12.3 g of bis-[(5-phenyl-imidazol-4-yl)-methyl]-ether dihydrochloride which is recrystallized from 96% ethanol to give a pure product, m.p. 215°–220° C. (dec.).

EXAMPLE 7

4-phenoxymethyl-5-(4-chlorophenyl)-imidazole hydrochloride

A solution of 15.2 g (0.16 mole) of phenol in 50 ml of ethanol is added to a solution of sodium ethylate in ethanol prepared from 3.7 g (0.16 mole) of sodium and 300 ml of ethanol. The reaction mixture is stirred at room temperature for 2.5 hours, then is cooled to −18° C./−15° C.

A solution of 21.1 g (0.08 mole) of 4-chloromethyl-5-(4-chlorophenyl)-imidazole hydrochloride in 500 ml of ethanol is added dropwise under stirring and while the temperature is maintained at about −10° C. The reaction mixture is allowed to stand at room temperature overnight, then is filtered and the filtrate is evaporated under reduced pressure.

The obtained residue is shaken with ether and with an amount of hydrochloric acid suitable to give a solution. The aqueous layer is separated and washed again with ether, then it is made basic with a concentrated solution of NH4OH and cooled.

The suspension is extracted several times with ethyl ether; the combined ethereal extracts are washed with water, dried on MgSO4, decolourized with activated carbon, filtered and evaporated.

The residue is crystallized from 100 ml of a mixture of isopropanol/hexane (24/100 v/v). After cooling to about 0° C., 13.2 g (yield 57.9%) of the free base is obtained; the hydrochloride thereof is prepared by evaporating to dryness the alcoholic solution of the base strongly acidified with an ethanolic solution of hydrochloric acid.

Two crystallizations from water give 10.4 g (yield 40.5%) of 4-phenoxymethyl-5-(4-chlorophenyl)-imidazole hydrochloride, m.p. 167°–168° C.

In a similar manner the following compounds have been prepared:
4-(4-chlorophenoxy)-methyl-5-(4-chlorophenyl)-imidazole hydrochloride, m.p. 188°–190° C.
4-(2-methylphenoxy)-methyl-5-(4-chlorophenyl)-imidazole hydrochloride, m.p. 166°–168° C.
4-(2,3-dimethylphenoxy)-methyl-5-(4-chlorophenyl)-imidazole hydrochloride, m.p. 182°–184° C.
4-(4-acetylaminophenoxy)-methyl-5-(4-chlorophenyl)-imidazole, m.p. 176°–178° C.
4-(2-methoxyphenoxy)-methyl-5-(4-chlorophenyl)-imidazole hydrochloride, m.p. 164°–167° C.
2-phenyl-4-phenoxymethyl-5-(4-chlorophenyl)-imidazole hydrochloride, m.p. 210°–215° C. (dec.).

What we claim is:

1. 4-phenoxy-methyl-5(4-chlorophenyl)-imidazole or a pharmaceutically acceptable acid addition salt thereof.

2. A pharmaceutical composition for analgesic, antipyretic or anti-inflammatory use containing an effective amount of a product of the formula

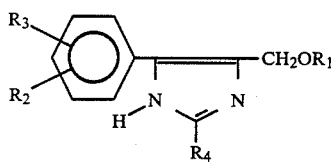

(I)

wherein
  $R_1$ is selected from the group consisting of a straight or branched chain alkyl having from 1 to 4 carbon atoms, cyclohexyl, benzyl, 5-phenyl-imidazole-4-yl-methyl, phenyl optionally substituted by chlorine, methyl, methoxy or acetamino,
  $R_2$ and $R_3$ are the same or different and each is selected from the group consisting of hydrogen, chlorine, methyl, methoxy, methylthio, methylsulfonyl,
  $R_4$ is hydrogen or phenyl, or of a pharmaceutically acceptable acid addition salt thereof together with a pharmaceutically acceptable carrier.

3. A pharmaceutical composition for analgesic, antipyretic or anti-inflammatory use containing an effective amount of a product of the formula

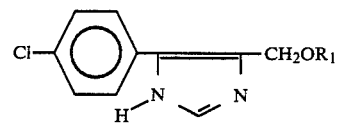

wherein
  $R_1$ is selected from the group consisting of a straight or branched chain alkyl having from 1 to 4 carbon atoms,
or of a pharmaceutically acceptable acid addition salt thereof together with a pharmaceutically acceptable carrier.

4. A pharmaceutical composition for analgesic, antipyretic or anti-inflammatory use containing an effective amount of 4-ethoxy-methyl-5-(4-chlorophenyl)-imidazole or of a pharmaceutically acceptable acid addition salt thereof together with a pharmaceutically acceptable carrier.

5. A pharmaceutical composition for analgesic, antipyretic or anti-inflammatory use containing an effective amount of 4-phenoxy-methyl-5-(4-chlorophenyl)-imidazole or of a pharmaceutically acceptable acid addition salt thereof together with a pharmaceutically acceptable carrier.

* * * * *